United States Patent
Yencho (12)

(10) Patent No.: US 7,001,402 B2
(45) Date of Patent: Feb. 21, 2006

(54) MEDICAL DEVICE HAVING MAGNETIC PROPERTIES

(75) Inventor: Stephen A. Yencho, Menlo Park, CA (US)

(73) Assignee: Cardica, Inc., Redwood City, CA (US)

(*) Notice: Subject to any disclaimer, the term of this patent is extended or adjusted under 35 U.S.C. 154(b) by 667 days.

(21) Appl. No.: 10/235,446

(22) Filed: Sep. 4, 2002

(65) Prior Publication Data

US 2004/0087983 A1 May 6, 2004

(51) Int. Cl.
*A61B 17/08* (2006.01)

(52) U.S. Cl. ...................................... 606/153

(58) Field of Classification Search ........... 606/153, 606/213, 215, 216; 252/62.51 R, 62.53, 252/62.54, 62.55, 62.58; 623/1.15
See application file for complete search history.

(56) References Cited

U.S. PATENT DOCUMENTS

| | | | | |
|---|---|---|---|---|
| 2,999,275 A | * | 9/1961 | Blume, Jr. ............... | 252/62.53 |
| 4,028,255 A | * | 6/1977 | Bolto et al. .............. | 252/62.54 |
| 4,873,504 A | * | 10/1989 | Blume et al. ............ | 252/62.54 |
| 6,352,543 B1 | | 3/2002 | Cole | |
| 6,491,842 B1 | * | 12/2002 | Bonnemann et al. .... | 252/62.55 |
| 6,555,018 B1 | * | 4/2003 | Sellers et al. ............ | 252/62.54 |
| 6,641,919 B1 | * | 11/2003 | Hayashi et al. .......... | 252/62.53 |
| 6,673,104 B1 | * | 1/2004 | Barry ....................... | 623/1.15 |

FOREIGN PATENT DOCUMENTS

| | | |
|---|---|---|
| WO | WO 01/17440 | 3/2001 |
| WO | WO 01/82803 A1 | 4/2001 |
| WO | WO 02/13698 A1 | 8/2001 |
| WO | WO 02/13703 A1 | 8/2001 |
| WO | WO 01/82803 | 11/2001 |
| WO | WO 02/13698 | 2/2002 |
| WO | WO 02/13699 | 2/2002 |
| WO | WO 02/13699 A1 | 2/2002 |
| WO | WO 02/13703 | 2/2002 |
| WO | WO 02/13704 | 2/2002 |
| WO | WO 02/13704 A1 | 2/2002 |

* cited by examiner

*Primary Examiner*—Julian W. Woo
(74) *Attorney, Agent, or Firm*—Brian A. Schar

(57) ABSTRACT

A high-energy density magnetic particulate is mixed with a biocompatible material to form a composite. The composite may be formed into a sheet, which may be rolled into a tube and laser-cut to form at least one medical device, such as one piece of a multi-piece anastomosis device. The device includes a number of interconnected struts, which may be sized such that any portion of the member placed in the bloodstream is substantially non-thrombogenic. A magnetic field is induced in the composite.

14 Claims, 2 Drawing Sheets

MEDICAL DEVICE HAVING MAGNETIC PROPERTIES

FIELD OF THE INVENTION

The present invention relates generally to medical devices, and more particularly to devices for performing anastomosis.

BACKGROUND

Anastomosis is a procedure where two separate tubular or hollow organs are surgically grafted together to form a continuous fluid channel between them. Vascular anastomosis between blood vessels creates or restores blood flow. When a patient suffers from coronary artery disease (CAD), an occlusion or stenosis in a coronary artery restricts blood flow to the heart muscle. In order to treat CAD, anastomosis is performed between a graft vessel and the affected coronary artery in order to bypass the occlusion and restore adequate blood flow to the heart muscle. This surgical procedure is known as coronary artery bypass grafting (CABG). Anastomosis may be performed in other surgical contexts, such as carotid artery bypass surgery or microvascular surgery.

Conventional anastomosis is performed by suturing two vessels together, which can be time-consuming and painstaking. More recently, magnetic anastomosis devices have been disclosed in U.S. Pat. No. 6,352,543. These devices are magnetic rings, where four rings are used to hold the end of a graft vessel to the side of a target vessel. High-energy magnets are used to enable these rings to hold tissue and maintain an anastomosis. However, high-energy density magnetic materials, such as samarium cobalt (e.g., $SmCo_5$, $Sm_2Co_{17}$, $SM_3Co_4$) and neodymium iron boron (e.g., $Nd_2Fe_{14}B$) tend to be brittle, and are prone to chipping or cracking in the manufacturing process. Neodymium iron boron also exhibits poor corrosion resistance. Thus, despite their useful magnetic properties, high-energy density magnetic materials pose challenges in manufacturing, and in ongoing use within a living body. Further, the magnetic rings disclosed in U.S. Pat. No. 6,352,543 place a relatively large amount of metal in direct contact with the bloodstream, increasing the risk of thrombosis, and potentially contributing to restenosis.

SUMMARY

In one aspect of the invention, high-energy density magnetic material is crushed, ground or otherwise processed into a particulate form, and mixed with a biocompatible material, such as a polymer. The biocompatible material is then cured or otherwise hardened or solidified. The high-energy density magnetic material is held within the matrix of biocompatible material to form a composite, such that the composite exhibits better handling qualities than the high-density magnetic material alone.

In another aspect of the invention, a magnetic field is induced in the individual particles of magnetic material within the matrix, such as by subjecting the composite material to an external magnetic field. As a result, the magnetic domains of the particles are substantially aligned such that the composite as a whole has a substantially uniform magnetic field. In this way, a magnetic field with desired properties can be generated by the magnetic particles held within the biocompatible matrix.

In another aspect of the invention, the composite may be formed into a sheet. The sheet may then be rolled into a tube or other desired shape. The tube is laser-cut to form at least one medical device, such as one piece of a multi-piece anastomosis device. In this way, existing equipment used to laser-cut stents, anastomosis devices and other devices from tubes of material can be adapted easily and at low cost to manufacture medical devices from a composite tube.

In another aspect of the invention, a composite tube is laser-cut to form an annulus having a major passage therethrough and a number of minor passages therein. By cutting minor passages into the annulus, a network of interconnecting members is formed, such that the annulus itself is formed from a plurality of interconnecting members. The dimensions of these members are chosen such that any portion of the annulus placed in the bloodstream is substantially non-thrombogenic.

BRIEF DESCRIPTION OF THE DRAWINGS

The use of the same reference symbols in different figures indicates similar or identical items.

DETAILED DESCRIPTION

Figure 1:
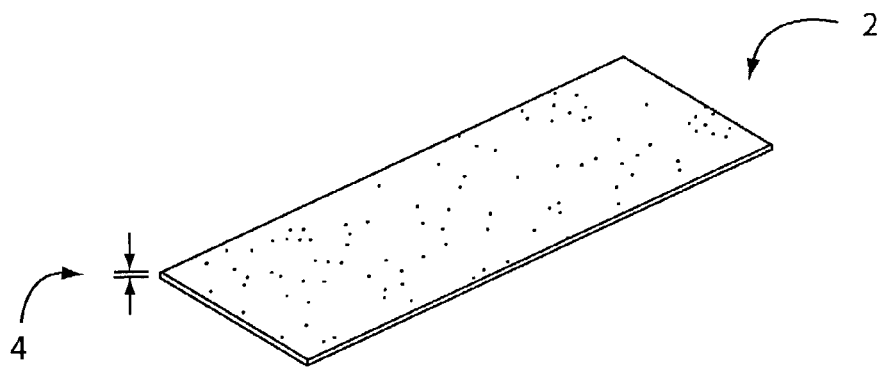
FIG. 1 is a perspective view of a sheet of biocompatible material with magnetic particles bound within it.

A medical device is constructed from a composite that includes a high-energy density magnetic material and a biocompatible substance such as a polymer.

A quantity of high-energy density magnetic material is provided. This high-energy density magnetic material may be samarium cobalt, neodymium iron boron, aluminum nickel cobalt, or other material. This material initially has a strong and/or uniform magnetic field. Alternately, this material does not have a strong and/or uniform magnetic field, due to a lack of alignment between the individual magnetic domains within the material.

This high-energy density magnetic material is then crushed, ground or otherwise processed into a particulate, such as a powder or aggregate. The average size of the constituent particles of the particulate is not critical to the invention. The particulate is created or sorted such that substantially none of the constituent particles of the particulate are larger than a selected size. However, the particulate may be produced such that the sizes of the individual particles forming the particulate are unconstrained. Alternately, the high-energy density magnetic material is initially provided in a particulate form, such as a powder or aggregate.

The high-energy density magnetic material in particulate form is then mixed with a biocompatible material, such as but not limited to a polymer. The specific type of biocompatible material used is not critical to the invention. The particulate may be treated with an agent to reduce surface tension, thereby allowing wetting by the biocompatible material. Such agents are standard. The mixing of the magnetic particulate with the biocompatible material may be performed when the biocompatible material is in a liquid, partially liquid or colloidal form. Advantageously, the magnetic particulate is mixed with the biocompatible material such that the magnetic particulate is substantially uniformly distributed within the biocompatible material. The mixture is then cooled or otherwise treated such that the biocompatible material solidifies by cooling, drying, curing or otherwise transitioning to a solid state. The result is a composite of magnetic particles within a biocompatible material, where the magnetic particles are held within a biocompatible matrix. Alternately, the biocompatible material is crushed, ground or otherwise formed into a particulate as well, and this particulate is mixed with the magnetic particulate. The mixture is then heated or otherwise treated such that the biocompatible material liquefies, then cooled or otherwise treated such that the biocompatible material solidifies, cures or otherwise transitions to form a composite with magnetic particulate held within a matrix of biocompatible material. Other or additional appropriate methods or techniques may be used to combine the magnetic particles with the biocompatible material.

In order to improve the biocompatibility of the composite still further, the magnetic particles may be coated with gold, gold alloy or other material before they are mixed with the biocompatible material. If coated magnetic particles are present at a surface of the composite material such that the biocompatible material does not cover those particles, the coating of the magnetic material and not the magnetic material itself is exposed to tissue. A standard vapor deposition process may be used to coat the particles with gold or other material.

Referring to FIG. 1, the composite material is formed into a sheet 2 having a thickness 4. The composite material may be formed in the configuration of the sheet 2. Such construction may be advantageous, as the thickness 4 of the sheet 2 may be selected in part to provide for rapid and/or efficient cooling or curing of the composite. Alternately, the composite may be formed in solid bricks, blocks, ingots, or other shapes, after which sheets 2 are individually sliced or cut therefrom, such as by laser cutting.

The sheet 2 can be manipulated, cut, formed, rolled, pressed, stamped, or otherwise acted upon to manufacture at least one component of a medical device. As an example, the sheet 2 can be used as the basis for manufacturing at least one element of a multi-element anastomosis device useful for coronary artery bypass graft (CABG) surgery, carotid artery bypass surgery, or other such surgical procedures. For such a use, at least a portion of the medical device may be located in the bloodstream. Where the medical device is to be placed at least partially in the bloodstream, the thickness 4 of the sheet 2 is advantageously equal to or less than 0.010 inches. The selected size of the largest particle within the particulate is preferably less than the thickness 4 of the sheet 2. In this way, the particles are sized such that the individual particles do not substantially extend out of any surface of the sheet 2.

Figure 2:
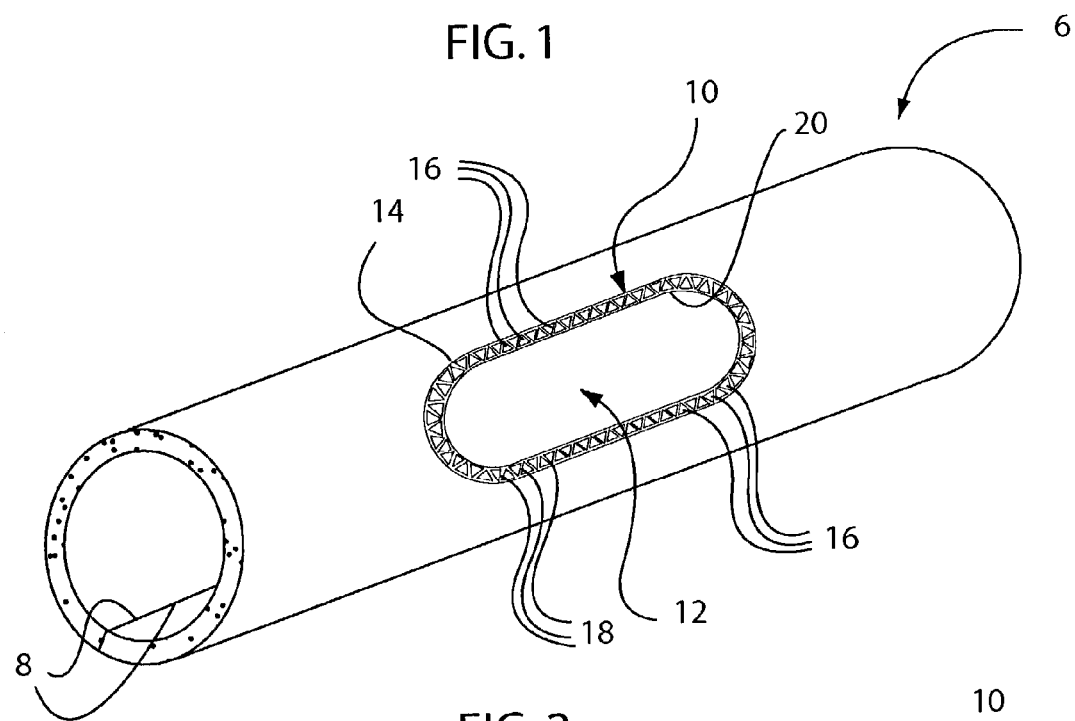
FIG. 2 is a perspective view of the sheet of FIG. 1 formed into a tube, with a medical device cut into it.

To construct at least one portion of an anastomosis device, the sheet 2 is rolled into a tube 6, as shown in FIG. 2, such that two edges 8 of the sheet 2 substantially abut one another. These edges 8 may be secured together, such as by adhesive, by melting them together, or by other structures, mechanisms and/or methods. The tube 6 may have a cross section that is substantially circular, substantially elliptical, complex, or shaped differently. The tube 6 may have a constant diameter along its length, or a variable diameter. Alternately, the edges 8 of the sheet 2 that abut one another in the tube 6 configuration are not secured together. Rather, the tube 6 maintains its tubular shape due to the stiffness of the sheet 2, by securing the sheet 2 to a mandrel or other fixture, or by other methods, structures and/or mechanisms. Alternately, the sheet 2 is rolled into a shape other than a tube 6 such that the edges 8 do not touch. Such a shape may have a semicircular cross-section, or other cross section. Alternately, the tube 6 is extruded or otherwise formed from a precursor shape, such as a thicker tube. Other methods may be utilized to form the tube 6 from the composite.

A laser is then used to cut material from the tube 6 to form a medical device 10. The use of a laser to cut stainless steel tubing into medical devices such as stents is standard in the art. The laser may be used in a way to cut the medical device 10 from the composite tube 6. Where the medical device 10 is one piece of an anastomosis device, a major passage 12 is cut within an outer perimeter 14 of the medical device 10, where the edge of the major passage 12 defines an inner perimeter 20 in the medical device 10. Thus, the medical device 10 is substantially an annulus bounded by the outer perimeter 14 and the inner perimeter 20, curved in a manner that corresponds to the curvature of the tube 6. Due to the curvature of the tube 6 from which it is cut, the annulus is not flat, and thus possesses a compound curvature. Alternately, the medical device 10 is shaped differently.

A number of minor passages 16 are also laser cut through the tube 6 between the outer perimeter 14 and the inner perimeter 20. These minor passages 16 are advantageously cut through the medical device 10 before the medical device 10 is cut from the tube 6, to simplify manufacturing. Although the minor passages 16 are shown having substantially triangular shapes, the minor passages 16 may be shaped differently, and may be slots, squares, diamonds, rectangles, polygons, circles, ovals, complex shapes, or any other shape. After the minor passages 16 have been cut, a number of members 18 remain, where the members 18 are defined between adjacent minor passages 16, between the minor passages 16 and the outer perimeter 14, and between the minor passages 16 and the inner perimeter 20.

The tube 6 is then placed in a magnetic field. The magnetic field is strong enough to cause the individual magnetic domains within the particulate in the composite material to align with one another. As a result, a magnetic field is induced in the tube 6 and the medical device 10. The external magnetic field applied to the tube 6 is oriented relative to the tube 6 such that the magnetic polarity of the medical device 10 is in a desired direction. By placing the tube 6 in the external magnetic field after the passages 12, 16 have been cut into it, the effects of heat and/or mechanical stress associated with that cutting do not affect the magnetic field of the tube 6 itself. Alternately, the tube 6 is placed in a magnetic field before the major passage 12 and/or at least one minor passage 16 is cut into the tube 6.

Figure 3:
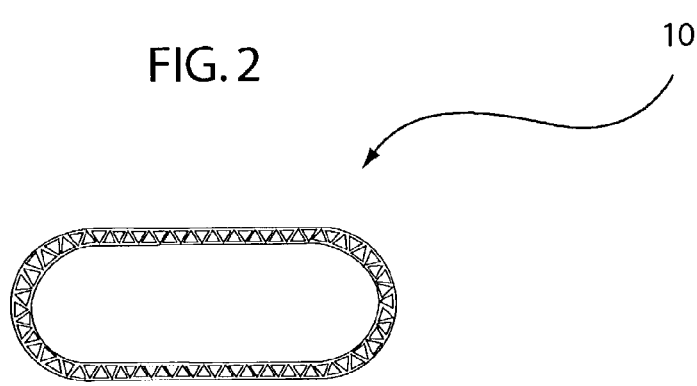
FIG. 3 is a top view of the medical device of FIG. 2.
Figure 4:
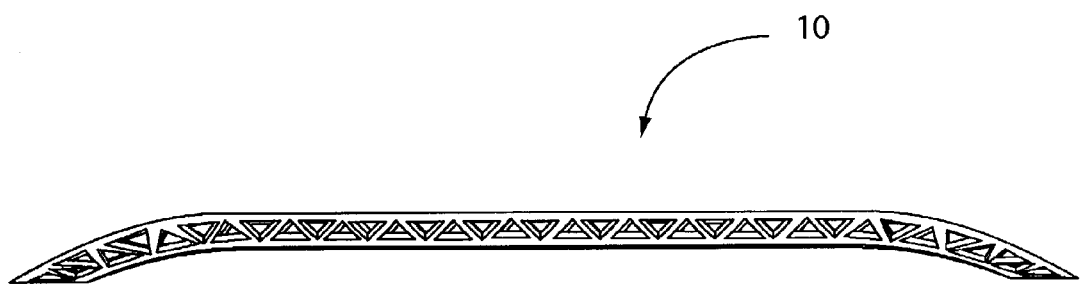
FIG. 4 is a side view of the medical device of FIG. 2.
Figure 5:
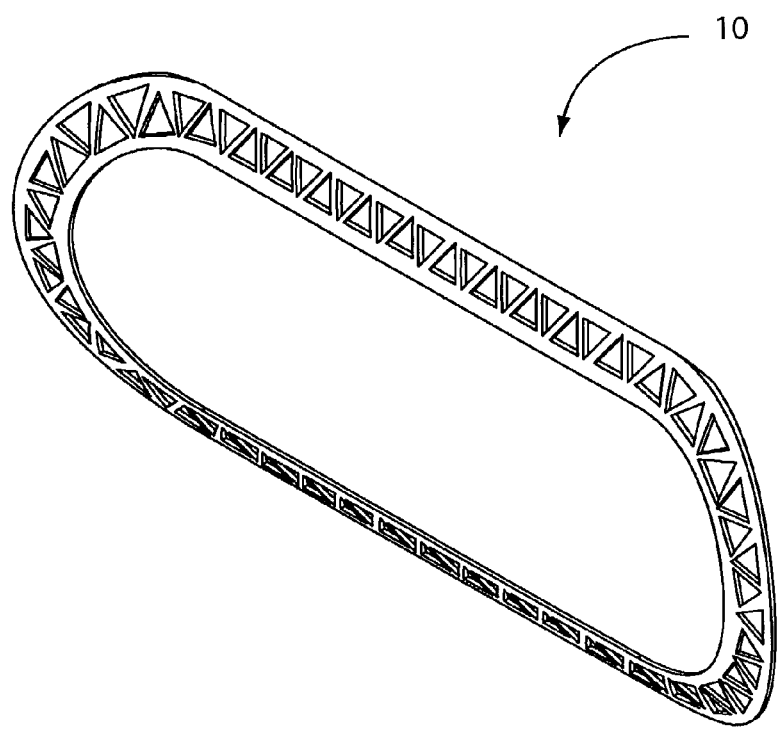
FIG. 5 is a perspective view of the medical device of FIG. 2.

Referring to FIGS. 3–5, the medical device 10 is then cut from the tube 6. The medical device 10 may then be ready for use, or may then be processed further. Alternately, the medical device 10 is cut from the tube 6 before a magnetic field is induced in it.

By cutting minor passages 16 into the medical device 10, a network of interconnected members 18 is formed. That is, as a result of cutting minor passages 16 into the medical device 10, the medical device 10 is formed from a number of interconnected members 18. Advantageously, the members 18 are sized such that they are substantially no larger than 0.010 inches in any dimension. For this reason, the thickness 4 of the sheet 2 is advantageously no larger than 0.010 inches, as described above. It is well established in the literature that members 18 of this size are less thrombogenic in the bloodstream. Thus, a medical device 10 substantially composed of a number of interconnected members 18 each no larger than 0.010 in any dimension can be placed, in whole or in part, in the bloodstream with minimal or no thrombogenic effects, if the material from which the members 18 are constructed is properly chosen. Examples of such a medical device 10 are stents, such as those commonly available in the United States and other countries.

Where the medical device 10 is a piece of a multiple-piece anastomosis device, the medical device 10 may be utilized in accordance with U.S. Pat. No. 6,352,543, which is hereby incorporated by reference in its entirety. As one example, four medical devices 10 formed by the method described above are provided. An end of a graft vessel is placed through the major passage 12 of one medical device 10 and everted. A second medical device 10 is placed against the everted end of the graft vessel, such that magnetic attraction pulls the medical devices 10 together and thereby holds the everted end of the graft vessel securely therebetween. A third medical device 10 is placed within a target vessel, such that the major passage 12 of the medical device 10 is aligned with an opening in the target vessel. A fourth medical device 10 is placed against the outside wall of the target vessel, such that magnetic attraction pulls the medical devices 10 together and secures them against the wall of the target vessel. That is, the area of the target vessel in proximity to the opening therein is held between two medical devices 10. As the end of the graft vessel is moved in proximity to the wall of the target vessel, magnetic attraction causes the medical device 10 placed against the outer wall of the target vessel to contact and hold the medical device 10 placed against the everted end of the graft vessel. The anastomosis is thereby completed.

While the invention has been described in detail, it will be apparent to one skilled in the art that various changes and modifications can be made and equivalents employed, without departing from the present invention. It is to be understood that the invention is not limited to the details of construction and/or the arrangements of components set forth in the above description or illustrated in the drawings. Therefore, the invention is not to be restricted or limited except in accordance with the following claims and their legal equivalents.

What is claimed is:

1. A method of manufacturing a medical device, comprising:

providing a high-energy density magnetic material in particulate form;

combining said particulate with a biocompatible material to form a composite;

inducing a magnetic field in said composite;

forming said composite into a sheet; and rolling said sheet into a tube.

2. The method of claim 1, wherein said providing includes crushing a high-energy density magnetic material into a particulate.

3. The method of claim 1, wherein said high-energy density magnetic material is samarium cobalt.

4. The method of claim 1, wherein said high-energy density magnetic material is neodymium iron boron.

5. The method of claim 1, wherein said particulate includes plurality of constituent particles, further comprising coating said constituent particles of said particulate with gold.

6. The method of claim 1, wherein said combining comprises:

mixing said particulate with biocompatible material in a substantially liquid state to form a mixture; and transitioning said mixture to a substantially solid state.

7. The method of claim 6, wherein said transitioning comprises cooling said mixture.

8. The method of claim 6, wherein said transitioning comprises drying said mixture.

9. The method of claim 6, wherein said transitioning comprises curing said mixture.

10. The method of claim 1, wherein said inducing comprises placing said composite in a magnetic field.

11. The method of claim 1, further comprising cutting said tube.

12. The method of claim 11, wherein said cutting is performed with a laser.

13. The method of claim 11, wherein said inducing is performed after said rolling.

14. The method of claim 11, wherein said inducing is performed after said cutting.

* * * * *